US00PP34293P2

(12) United States Plant Patent
Werner et al.

(10) Patent No.: US PP34,293 P2
(45) Date of Patent: Jun. 7, 2022

(54) ***CERCIS* TREE NAMED 'NC2017-108'**

(50) Latin Name: *Cercis canadensis*
Varietal Denomination: NC2017-108

(71) Applicant: North Carolina State University, Raleigh, NC (US)

(72) Inventors: Dennis James Werner, Raleigh, NC (US); Leanne Marie Kenealy Atkins, Abingdon, VA (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/574,094

(22) Filed: Jan. 12, 2022

(51) Int. Cl.
*A01H 5/00* (2018.01)

(52) U.S. Cl.
USPC ..... Plt./216

(58) Field of Classification Search
USPC ..... Plt./216
See application file for complete search history.

*Primary Examiner* — Annette H Para
(74) *Attorney, Agent, or Firm* — Myers Bigel, P.A.

(57) ABSTRACT

'NC2017-108' is a new and distinct variety of redbud tree that has the following unique combination of desirable features that are outstanding in a new variety including (1) ease of asexual propagation using chip budding, (2) semi-upright growth habit; (3) foliage with glossy green color; (4) white double flowers produced in abundance during the spring; and female structures that are essentially sterile, resulting in no seed pod set.

2 Drawing Sheets

Latin name of the genus and species: The Latin name of the novel plant variety disclosed herein is *Cercis canadensis*.

Variety denomination: The inventive variety of the *Cercis canadensis* disclosed herein has been given the varietal denomination 'NC2017-108'.

BACKGROUND OF THE INVENTION

The present invention comprises a new and distinct hybrid cultivar of *Cercis canadensis* herein referred to by the cultivar name 'NC2017-108'. Ornamental redbud 'NC2017-108' (*Cercis canadensis*) was derived from a controlled hybridization of *Cercis canadensis* 'Dwarf White' (white single flowers) (unpatented) and *Cercis canadensis* 'Flame' (double purple flowers) (unpatented). 'Dwarf White' was a chance seedling that was discovered in cultivation in Charleston, Ill. by the late Dr. Wesley Whiteside, Professor Emeritus of Botany, Eastern Illinois University. Dr. Whiteside shared plants of 'Dwarf White' with J. C. Raulston, faculty member and Director of the North Carolina State University Arboretum (now JC Raulston Arboretum (JCRA)) in 1988, and Dr. Raulston established this variety in the JCRA collection at that time. 'Flame' is an old cultivar discovered in the early 1900's in the U.S. Midwest. It was obtained by the JCRA from a nursery in Aiken, S.C. in 1988. The goal of the controlled hybridization was to develop a redbud showing double, white flowers. Double flowers provide distinct ornamental value and are essentially female sterile. Hence, no unsightly seed pods are formed, an asset in the landscape. 'NC2017-108' will be an excellent companion to 'Pink Pom Poms', a double-pink-flowered cultivar (U.S. Plant Pat. No. 27,630).

The original controlled hybridization to obtain $F_1$ seed was made by hand in March 1999 in Raleigh, N.C. 'Dwarf White' (JCRA accession number 020083) was used as the female parent, as trees of 'Flame' are female sterile. Pollen was obtained from 'Flame' (JCRA accession number 880370) from flowers of the existing tree in the JCRA collection. $F_1$ seed from the controlled hybridization was harvested in August 1999. Seed set was very low, and only two seeds were obtained. After harvest, seeds were acid scarified for 30 minutes in concentrated sulfuric acid, rinsed thoroughly, and subsequently cool-stratified for about 12 weeks in the fall of 1999 to satisfy the seed chilling requirement. Seeds were sown in January 2000 under greenhouse conditions. The two $F_1$ hybrid seedlings were initially grown in the greenhouse for about 4 months, and then subsequently transplanted to larger pots and grown in a research plot in summer 2000. Plants were moved to a permanent field location in Jackson Springs, N.C. in winter 2001, and designated with selection numbers 'NC99-6-1' and 'NC99-6-2'. Both $F_1$ seedlings showed purple, double flowers similar to the male parent when they eventually flowered in 2003.

Because 'NC99-6-1' and 'NC99-6-2' were both female sterile, development of a $F_2$ family was not possible. Hence, a backcross strategy hybridizing the $F_1$ trees as males to a single-flowered white parent, was employed in an attempt to recover double-flowered white offspring. Backcross hybridizations were conducted in March 2014 in a greenhouse using potted trees. The single-flowered white parent chosen for the backcross hybridization was 'Royal White' (unpatented). This cultivar was chosen to reduce the potential for inbreeding depression, as it differs genetically from 'Dwarf White' that was used to create the original $F_1$ family. To accomplish the backcross, pollen was obtained and bulked from both $F_1$ selections (male parent) and crossed onto 'Royal White' (essentially female parent). Backcross seed was harvested in August 2014. Seed was acid scarified followed by cool stratification for about 3 months beginning fall 2014. Stratified backcross seed was sown December 2014, germinated, and seedlings were grown in the greenhouse during spring/summer 2015. Thirty-six backcross seedlings subsequently were transplanted into the field at the Jackson Springs, N.C. in November 2015. The trees first flowered in 2017. Of the 35 trees, 12 trees showed double, white flowers. The remaining trees were discarded. Over 4 years of observation, all 12 selections were evaluated for flower density, flower size, cold hardiness (lack of trunk winter injury), and tree architecture. 'NC2017-108' was chosen as the superior selection based on these criteria.

Propagules of the 'NC2017-108' selection were sent to Belvidere, Tenn. in August 2018 for initial propagation and nursery trials by chip budding onto seedling rootstocks of *Cercis canadensis*. Five trees were propagated. This was the first asexual propagation of 'NC2017-108' and all trees maintained their true-to-type identity when asexually propagated in this manner. During all asexual propagation, the characteristics of the original plant have been maintained. Plants derived from chip budding exhibit characteristics identical to those of the original plant, and no aberrant phenotypes have appeared.

SUMMARY OF THE INVENTION

'NC2017-108' has excellent vigor and shows a distinct semi-upright habit (FIG. 1). Leaves are dark green, and typical of *C. canadensis*. Flowers are white, fully double, with up to 24 petals per flower (5 petals is typical for redbud) (FIG. 2). Flower production is heavy. Flowers are essentially female sterile; hence no fruit (seed) pods are formed. Flowering is typically about 7-10 days after the usual flowering time of redbud. Leaves remain attractive throughout the growing season and show very limited leaf spot or necrosis, often problematic of redbud in NC. In a production nursery setting, trees demonstrate excellent vigor and branching, and can be routinely propagated by chip budding.

BRIEF DESCRIPTION OF THE DRAWINGS

This new redbud is illustrated by the accompanying photographs which show the plant's foliage and inflorescences. The colors shown are as true as can be reasonably obtained by conventional photographic procedures. Colors in the photographs may differ slightly from the color values cited in the detailed botanical description, which accurately describe the colors of the new redbud.

DETAILED BOTANICAL DESCRIPTION

Figure 1:
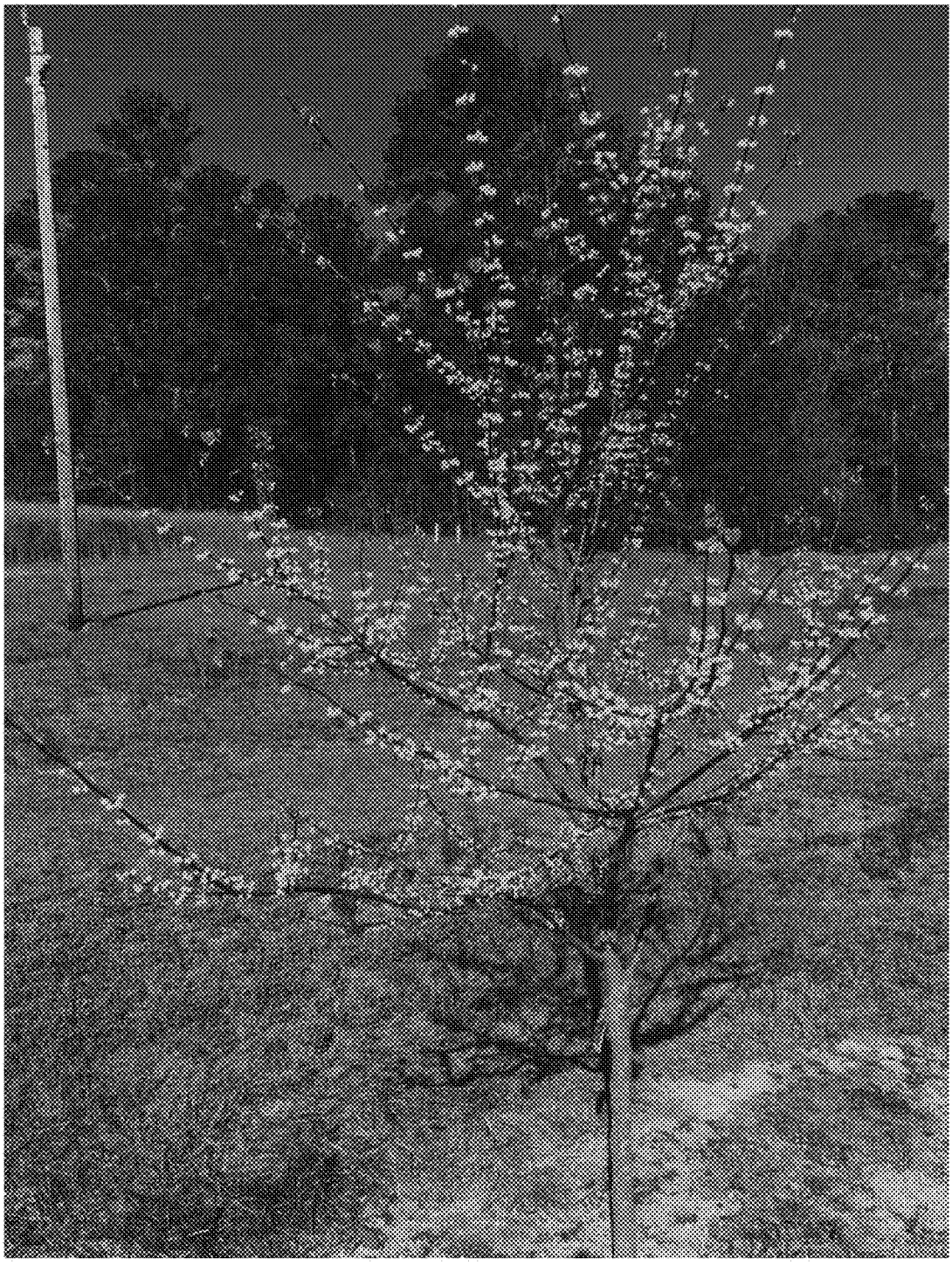
FIG. 1 is a color photograph showing a three-year-old original tree of 'NC2017-108' showing prolific flower production, semi-upright architecture, and excellent branching. Photo taken Apr. 10, 2019, in Jackson Springs, N.C.
Figure 2:
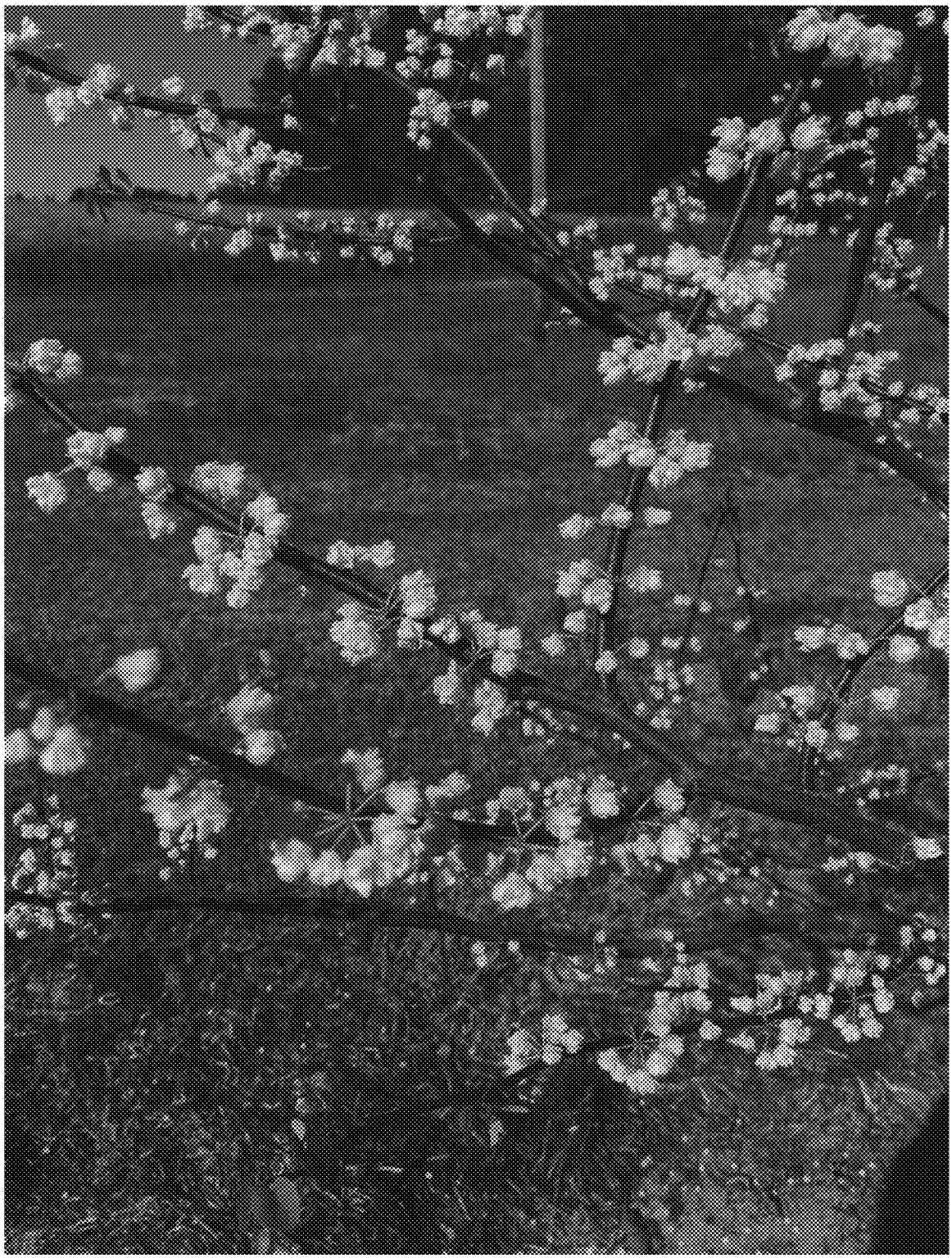
FIG. 2 is a color photograph showing prolific production of double white flowers on 'NC2017-108'. Photo taken Apr. 10, 2019, in Jackson Springs, N.C.

The following is a detailed description of the botanical characteristics of the new and distinct variety of the redbud tree known by the denomination 'NC2017-108'. The detailed description was taken on three-year old to four-year old trees in Jackson Springs, N.C. All colors cited herein refer to The Royal Horticultural Society Colour Chart (The Royal Horticultural Society (R.H.S.), London, 2007 Edition). Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name.*—*Cercis canadensis* 'NC2017-108'.
*Common name.*—Redbud.
*Type of plant.*—Deciduous, perennial tree.
Parentage: 'Royal White' x (NC99-6-1, NC99-6-2, pollen bulk).

Plant description:

*Plant habit.*—Semi-upright.
*Height.*—7.9 ft. high (5-year-old tree).
*Spread.*—7.1 ft. wide (5-year-old tree).
*Branching habit.*—well-branched.

Trunk:

*Diameter.*—10.1 cm. at 30.5 cm. above the ground.
*Bark surface.*—Rough.
*Color.*—Grey-green (198A).

Stems:

*Stem growth pattern.*—Slightly zig-zag (deviating less than 5 degrees from vertical at each node).
*Color* (*current season's growth*).—Green (143B).
*Color* (*one-year previous season's growth*).—Brown (N200B).
*Shape.*—Circular.
*Diameter.*—4 mm on new growth.
*Length* (*one year old shoots*).—51 cm to 64 cm.
*Internode length* (*one-year-old dormant shoots*).—3.5 cm to 4.1 cm.
*Surface.*—Slightly rugose.
*Lenticels.*—Numerous, about 1 mm or less), circular to slightly elongate, grey-brown (199C).

Foliage:

*Type.*—Deciduous.
*Leaf arrangement.*—Alternate.
*Leaf shape.*—Cordate.
*Leaf venation.*—Reticulate.
*Leaf surface.*—Slightly rugose (adaxial and abaxial) (both mature and immature leaves).
*Leaf margin.*—Entire.
*Leaf attachment.*—Petiolate.
*Leaf length.*—9.4 cm to 11 cm (to base of sinus) and 11.5 cm to 13 cm (to end of lobe).
*Leaf width.*—11.5 cm to 12.5 cm (widest portion).
*Sinus indentation.*—0.8 cm to 2.7 cm.
*Leaf tip.*—Distinctly pointed.
*Leaf base.*—Cordate.
*Margin type.*—Entire.
*Leaf color.*—Immature: Adaxial: Green (137B). Abaxial: Green (138B). Mature: Adaxial: Green (137B). Abaxial: Green (138B).
*Leaf attachment.*—Petiolate.
*Stipules.*—Petiolate.
*Petiole diameter.*—2 mm.
*Petiole length.*—3.2 cm to 3.8 cm.
*Petiole shape.*—Round.
*Petiole color.*—Green 143A.
*Petiole surface.*—Smooth, no pubescence.

Flowers:

*Flowering season.*—Early April in in central North Carolina, for about 1-2 weeks depending on the temperature.
*Symmetry.*—Radial symmetry (vs. typical bilateral symmetry of redbud).
*Flower type.*—Papillonaceous (pea-like), but with atypical form and petal number.
*Inflorescence form.*—Fasicle.
*Number of flowers per cluster.*—4 to 6.
*Flower arrangement.*—Sessile clusters.
*Location.*—Nodes of previous year's growth, and along older stems and trunk (cauliflory).

*Length of bloom*.—About 1 to 2 weeks, depending on the temperature.
*Flower length* (*at full bloom*).—8 mm to 10 mm.
*Flower width* (*across wings at anthesis*).—8 mm to 9 mm.
*Flower depth* (*bottom of keel petals to top of wings*).—NA.
*Pedicel length*.—9 to 12 mm.
*Pedicel diameter*.—Less than 1 mm.
*Pedicel shape*.—Round.
*Pedicel color*.—Green group 142C.
*Pedicel surface*.—Smooth.
*Fragrance*.—Not detected.

Flower bud:
*Shape*.—Slightly elongate to broad oval.
*Color*.—Brown group 200B.
*Surface*.—Smooth.
*Diameter*.—2 mm to 3 mm.
*Length*.—2 mm.

Petals:
*Number*.—17 to 24.
*Color*.—White (NN155D).
*Petal surface*.—Smooth (both surfaces).
*Petals fused or unfused*.—Fused.
*Petal margin*.—Entire.

Calyx:
*Shape*.—Vase.
*Length*.—2 mm to 3 mm.
*Diameter*.—4 mm to 5 mm.
*Color*.—Green (142B).
*Surface* (*inner and outer*).—Smooth.

Sepals:
*Number*.—1 fused.
*Color*.—Green (142B).
*Surface*.—Rough.

Reproductive organs:
*Pistil*.—Often malformed and distorted. Length 3 mm to 5 mm; width less than 1 mm. Surface: Smooth. Number: 1.
*Stigma*.—Shape: Round to slightly oval. Length: Less than 1 mm. Width: Less than 1 mm. Color: Green group (142D).
*Style*.—Shape: Round to slightly flattened. Length: 2 mm to 4 mm. Width: Less than 1 mm. Color: Green group (142D).

Stamens:
*Number*.—Rarely develop. Malformed if present.
*Fused or unfused at the base*.—Unfused.
*Length*.—Malformed, largely absent.
*Width*.—Malformed.
*Color* (*filament*).—None present.

Anthers:
*Shape*.—Very rarely formed. When noted, found at tip of petal.
*Length*.—Malformed.
*Width*.—Malformed.
*Color*.—None present.

Pollen:
*Color and amount*.—Too sparse to characterize.

Ovary:
*Superior position*.—Superior.
*Shape*.—Elongate.
*Length*.—Less than 1 cm.
*Width*.—Less than 1 cm.
*Color*.—Green group (142D).

Seed and fruit: No pods or seed produced in four years of observation.

Disease and insect resistance: No significant disease or insect pests have been observed.

Cold hardiness: Confirmed in 7a, 6a anticipated.

COMPARISON WITH PARENTAL PLANTS

Regarding comparisons to its parents and other related cultivars, 'NC2017-108' differs from its grandparent 'Flame' in having double white flowers, in contrast to the double purple flowers of 'Flame' and differs from its grandparent 'Dwarf White' in having double white flowers in contrast to the single white flowers of 'Dwarf White'. 'NC2017-108' differs from its female parent 'Royal White' in having double white flowers in contrast to the single white flowers of 'Royal White' and from its male parents NC99-6-1 and NC99-6-2 (pollen bulked) in having double white flowers, in contrast to the double purple flowers of NC99-6-1 and NC99-6-2.

'NC2017-108' differs from its closest near relative, half-sib 'Pink Pom Poms' (U.S. Plant Pat. No. 27,630) (both have 'Flame' redbud as a common parent), in having double white flowers in contrast to the double pink flowers of 'Pink Pom Poms'.

What is claimed is:

1. A new and distinct variety of redbud tree (*Cercis*) named 'NC2017-108' having the characteristics substantially as described and illustrated herein.

* * * * *